United States Patent
Yokoyama et al.

(10) Patent No.: US 8,252,362 B2
(45) Date of Patent: Aug. 28, 2012

(54) METHOD OF MEASURING COATING QUANTITY AND METHOD OF PREDICTING DISSOLUTION BEHAVIOR

(75) Inventors: Makoto Yokoyama, Gifu (JP); Koji Ukai, Gifu (JP)

(73) Assignee: Eisai R&D Management Co., Ltd., Tokyo (JP)

(*) Notice: Subject to any disclaimer, the term of this patent is extended or adjusted under 35 U.S.C. 154(b) by 1027 days.

(21) Appl. No.: 11/794,763

(22) PCT Filed: Feb. 2, 2006

(86) PCT No.: PCT/JP2006/002200
§ 371 (c)(1),
(2), (4) Date: Jul. 5, 2007

(87) PCT Pub. No.: WO2006/083001
PCT Pub. Date: Aug. 10, 2006

(65) Prior Publication Data
US 2009/0269484 A1    Oct. 29, 2009

(30) Foreign Application Priority Data
Feb. 3, 2005  (JP) ................ 2005-027417

(51) Int. Cl.
*C23C 14/54* (2006.01)
(52) U.S. Cl. ............... 427/10; 428/403; 428/64; 428/65; 428/426; 428/411.1; 428/913; 424/427; 427/8; 427/9; 427/2.14; 427/457; 427/595
(58) Field of Classification Search .................... 428/64, 428/403; 427/8, 9, 10
See application file for complete search history.

(56) References Cited

U.S. PATENT DOCUMENTS

| | | | | |
|---|---|---|---|---|
| 5,110,648 A | * | 5/1992 | Suzuki et al. | 428/64.8 |
| 5,679,955 A | | 10/1997 | Schmidt et al. | |
| 6,638,973 B2 | * | 10/2003 | Holton | 514/468 |
| 6,690,015 B1 | | 2/2004 | Benes et al. | |
| 2005/0208303 A1 | * | 9/2005 | Atarashi et al. | 428/403 |

FOREIGN PATENT DOCUMENTS

JP   61-66115 A   4/1986
(Continued)

OTHER PUBLICATIONS

Li Duan et al., Studies on Bioavailability of Sustained Release Indomethacin Capsules, Acta Pharmaceutica Sinica, 1985, pp. 387-391, vol. 20, No. 5, China Academic Journal Electronic Publishing House.

(Continued)

*Primary Examiner* — Dah-Wei Yuan
*Assistant Examiner* — Andrew Bowman
(74) *Attorney, Agent, or Firm* — Birch, Stewart, Kolasch & Birch, LLP

(57) ABSTRACT

Evaluation methods that employ the near infrared spectrum have generally had a low specificity and in particular have encountered difficulty in the evaluation of trace components, and the accurate measurement of coating quantity by methods using the near infrared spectrum has been quite problematic. The quantity of coating applied to a coating target, such as granules or uncoated tablets, is measured based on the absorption or scattering of light in the 800 to 1100 nm wavelength region by an additive coated on the coating target. The use of polyethylene glycol or a long-chain hydrocarbyl-containing compound as the additive is preferred.

5 Claims, 5 Drawing Sheets

FOREIGN PATENT DOCUMENTS

| | | |
|---|---|---|
| JP | 1-221662 A | 9/1989 |
| JP | 6-27019 A | 2/1994 |
| JP | 8-178842 A | 7/1996 |
| JP | 9-113441 A | 5/1997 |
| JP | 11-248624 A | 9/1999 |
| JP | 2002-530664 A | 9/2002 |
| JP | 2002-538432 A | 11/2002 |
| WO | WO-00/31499 A1 | 6/2000 |

OTHER PUBLICATIONS

Lu Jia-Hui et al., Rapid Determination of Ethanol in Wine by Short-wavelength Near-infrared Spectroscopy, Journal of JLN University (Science Edition), Apr. 2002, pp. 245-247, vol. 41, No. 2, China Academic Journal Electronic Publishing House.

Keiso, vol. 48, No. 1, Jan. 2005, pp. 62-65.

Andersson et al., "Quantitative Analysis of Film Coating in a Fluidized Bed Process by In-Line NIR Spectrometry and Multivariate Batch Calibration," Analytical Chemistry vol. 72, No. 9, May 1, 2000, pp. 2099-2108.

Zannikos et al., "Spectrophotometric Prediction of the Dissolution Rate of Carbamazepine Tablets," Pharmaceutical Research, vol. 8, No. 8, Feb. 25, 1991, pp. 974-978.

Chinese Patent Office Communication (1st OA), dated Jan. 9, 2009, for corresponding application CN 200680002747.

Chinese Patent Office Communication (2nd OA), dated Aug. 7, 2009, for corresponding application CN 200680002747.

English Language Translation of JP 01-221662A (Publication date: Sep. 5, 1989).

English Language Translation of JP 06-27019A (Publication date: Feb. 4, 1994).

English Language Translation of JP 08-178842A (Publication date: Jul. 12, 1996).

English Language Translation of JP 11-248624A (Publication date: Sep. 17, 1999).

English Language Translation of JP 61-66115A (Publication date: Apr. 4, 1986).

Japanese Patent Office Communication, dated Feb. 1, 2011, for corresponding application JP 2007-501681.

Li et al., Studies on Bioavalability of Sustained Release Indomethacin Capsules, Acta Pharmaceutica Sinica, 1985, vol. 20, No. 5, pp. 387-391.

Lu et al., Rapid Determination of Ethanol in Wine by Short-Wavelength Near-Infrared Spectroscopy, Journal of JiLin University (Science Edition), Apr. 2003, vol. 41, No. 2, pp. 245-247.

Response, filed Mar. 31, 2011, to Office Action dated Feb. 1, 2011 in JP 2007-501681.

Response, filed May 25, 2009, to first Office Action in CN 200680002747.

Response, filed Oct. 21, 2009, to second Office Action in CN 200680002747.

Yokoyama, Need and Problem of Near-Infrared Spectrometer in Manufacturing Process of Pharmaceutical Drug, Keiso, vol. 43, No. 1, Jan. 2005, pp. 62-65.

* cited by examiner

METHOD OF MEASURING COATING QUANTITY AND METHOD OF PREDICTING DISSOLUTION BEHAVIOR

TECHNICAL FIELD

The present invention relates to a method of measuring the coating quantity when a coating liquid is applied to granules, tablets or the like, the measurement being carried out using the absorption or scattering of light in the 800 to 1100 nm wavelength range by an additive that has been coated on a coating target, and relates to a method of predicting the dissolution behavior of a pharmacologically effective component from the granules or the like, based on the coating quantity determined by the aforementioned method.

RELATED ARTS

Various single- or multilayer coatings may be applied to oral formulations, such as granules or tablets, for the purpose of, for example, quality preservation, taste masking, or controlling the dissolution properties, e.g., enteric dissolution behavior, sustained-release behavior. Such coatings are typically applied by a method such as film coating, powder coating, or press coating. Since slight differences in coating quantity have an influence on, for example, the characteristics of a formulation, quality, and so forth, it is necessary from a quality management perspective to exercise fairly rigorous control on the quantity of a coating on the coating target, e.g., granules or uncoated tablets.

A method heretofore used to measure the coating quantity comprises determining the coating quantity from the average weight of a formulation taken before and after the coating process.

Evaluation of the dissolution behavior is generally carried out in the form of a dissolution test or disintegration test using, for example, the actual tablets. These evaluation methodologies, being destructive tests, cannot be carried out on all of a test material. A paper by Martin et al. (Nonpatent Reference 1) and a paper by Peter et al. (Nonpatent Reference 2), for example, are known with regard to technologies for overcoming these problems. Nonpatent Reference 1 relates to an in-line methodology that employs the near infrared spectrum to measure the thickness of a coating layer applied on a pellet. Nonpatent Reference 2 discloses results that suggest the possibility of being able to predict the dissolution behavior of carbamazepine tablets by measurement of the near infrared spectrum.

Nonpatent Reference 1

Martin Andersson et al., "Quantitative Analysis of Film Coating in a Fluidized Bed Process by In-Line NIR Spectrometry and Multivariate Batch Calibration" Anal. Chem. 2000, 72, 2099-2108.

Nonpatent Reference 2

Peter N. Zannikos et al., "Spectrophotometric Prediction of the Dissolution Rate of Carbamazepine Tablets" Pharmaceutical Research, 1991, 8, 974-978.

DISCLOSURE OF THE INVENTION

The method of determining of coating quantity from the average weight of a formulation taken before and after the coating process carries out measurement after the measurement sample has been collected and is therefore unable to measure real-time changes in the coating quantity during production. Moreover, drug products employ a variety of ingredients other than the drug component itself, and the absorptions from various components overlap in the near infrared region where absorption for the molecular vibration of, for example, C—H, N—H, and O—H, is observed. Methods of evaluation that employ the near infrared spectrum therefore generally have a low specificity and in particular encounter difficulty in the evaluation of trace components. As a consequence, while there are some reports (Nonpatent References 1 and 2) of the use of near infrared spectroscopic measurements to evaluate coating quantity and predict dissolution behavior, this has not grown into an all-purpose technology for the detection of coating quantity. The technology of Nonpatent Reference 1 in fact uses the near infrared in the long wavelength region (1100 to 2500 nm) of the near infrared region for its measurement wavelength. Absorption in the wavelength region has a stronger intensity than in the low wavelength region (400 to 1100 nm). However, since this is a region next to fundamental vibrations, there is a high possibility of overlap by combination tones of various vibrations and first and second overtones. The problem of a poor specificity therefore arises. The long wavelength region (1100 to 2500 nm) of the near infrared is again used in Nonpatent Reference 2, and this report is also limited to the use of carbamazepine tablets as the measurement target.

As a result of intensive and extensive investigations directed to solving the problems identified above, the inventor of the present application unexpectedly discovered that the coating quantity can be very accurately measured, with little influence from interference due to peaks based on other components, by measurement using the 800 to 1100 nm wavelength region of the near infrared spectrum of, for example, granules or tablets coated with a coating liquid that contains, for example, polyethylene glycol and/or a long-chain hydrocarbyl-containing compound.

The present invention provides a method of measuring the quantity of a coating applied to a coating target, based on a measurement value obtained by measuring the absorption or scattering of light in the 800 to 1100 nm wavelength range by an additive coated on the coating target.

The present invention additionally provides a method of predicting the dissolution behavior of a pharmacologically effective ingredient from a coating target, based on the coating quantity obtained by the aforementioned method of coating quantity measurement.

The present invention further provides a method of measuring the quantity of a coating applied to a coating target, based on the absorption or scattering of light in the 800 to 1100 nm wavelength range by an additive coated on the coating target.

DETAILED DESCRIPTION OF THE INVENTION

The present invention can use any additive that absorbs or scatters light in the 800 to 1100 nm wavelength range, for example, plasticizers, lubricants, fluidizers, colorants, stabilizers, masking agents, coating agents (coating material), and so forth. A long-chain hydrocarbyl-containing compound can be used as the additive. In the present invention, long-chain hydrocarbyl denotes a saturated or unsaturated hydrocarbon chain that contains at least 6 carbons, for example, cetyl, stearyl, and so forth. Long-chain hydrocarbyl-containing compounds can be exemplified by higher alcohols, fatty acid esters, and fatty acid salts. The higher alcohols can be specifically exemplified by tetradecanol, pentadecanol, cetyl alcohol, heptadecanol, nanodecanol, docosanol, and stearyl alcohol; the fatty acid esters can be specifically exemplified by glycerol/fatty acid esters and sodium stearyl fumarate; and the fatty acid salts can be specifically exemplified by magnesium stearate and calcium stearate. However, the long-chain hydrocarbyl-containing compounds usable by the invention of the present application are not limited to the preceding. Polyethylene glycol can also be used as the additive in the present invention. A variety of polyethylene glycols graded by molecular weight are commercially available, any of which may be used in the present invention. Among these, the use of Macrogol 4000, Macrogol 6000, Macrogol 20000, and so forth is preferred and the use of Macrogol 6000 is more preferred.

The present invention can be used regardless of the coating functionality as long as the coating liquid contains an additive that absorbs or disperses light in the 800 to 1100 nm wavelength region. For example, a taste-masking coating, gastric-dissolving coating, enteric-dissolving coating, sustained-release coating, other types of coatings in order to strengthen the chemical stability or physical strength of the formulation, and so forth can be used.

The near infrared radiation used by the present invention has a wavelength of 800 to 1100 nm. The wavelength preferred therein is 900 to 960 nm while 920 to 950 nm is more preferred. 920 to 940 nm is even more preferred when the evaluation is carried out using a long-chain hydrocarbyl-containing compound, while 930 to 950 nm is even more preferred when the evaluation is carried using polyethylene glycol. This near infrared radiation can be generated by a tungsten lamp, halogen lamp, or other known means. The detector used to detect this near infrared radiation can be a photoconductive detector of lead sulfide (PbS), a silicon (Si) photodetector, or another known detector. The present invention is directed to measurement of the coating quantity of a granule or tablet coating target based on the spectrum in the near infrared region; thus, in addition to measurement based on the absorption spectrum, the coating quantity can be measured, for example, based on the spectrum of the near infrared region present in Raman-scattered light.

The test material that can be measured by the present invention can be exemplified by tablets and granules (including microparticulate formulations) comprising a particulate material, such as a granule coating target or uncoated tablets, on which a coating has been executed by a method such as, for example, film coating, powder coating, or press coating. Moreover, due to the use of the low wavelength region (400 to 1100 nm) that is readily transmitted through the test material, the measurement method is not limited to diffuse reflection, transmission, and transmission reflection and other known techniques can also be used.

The calculation of the coating quantity and prediction of dissolution behavior are carried out in the present invention by the extraction from the near infrared region spectrum yielded by the test material of a mathematical relationship related to the coating quantity and the dissolution behavior. The techniques used to extract such a mathematical relationship encompass preprocessing of the spectrum (e.g., normalization, difference spectrum, second derivative), multivariate analysis (e.g., multiple linear regression or MLR, principal component analysis or PCA, partial least squares or PLS), and other methods obtained by known means.

Since the invention of the present application carries out measurement using light in the 800 to 1100 nm wavelength range, it is able to carry out measurement of the coating quantity with little influence from interference by spectra based on other ingredient components. In addition, the present invention, because its measurement wavelength range is limited to the low wavelength region, can shorten the time required for measurement and can also lower the cost of the measurement instrumentation by enabling the use as the light source and/or detector of commercially available devices that operate in the ultraviolet region.

EXAMPLES

Preferred embodiments of the invention of the present application are described in the following, but the invention of the present application is not limited thereby.

Test Example 1

Test of the Measurement of the Spectra of Various Ingredients

The near infrared absorption spectra in the near infrared region were measured on polyethylene glycol, long-chain hydrocarbyl-containing compounds, and various ingredients as used in pharmaceutical products. The measurement results are given in FIG. 4 in the neighborhood of the absorption region band for the fundamental vibrations based on long-chain hydrocarbyl groups; the results in the neighborhood of the absorption region band for first overtone vibrations are given in FIG. 3; the results in the neighborhood of the absorption region band for second overtone vibrations are given in FIG. 2; and the results in the neighborhood of the absorption region band for third overtone vibrations are given in FIG. 1. In these Figures, the measurement results are those of near-infrared spectrum treated by second derivative (secondary differential). Peaks due to the long-chain hydrocarbyl-containing compounds (1-tetradecanol, 1-pentadecanol, cetyl alcohol, 1-heptadecanol, stearyl alcohol, 1-nanodecanol, 1-docosanol, glycerol/fatty acid esters, magnesium stearate, and sodium stearyl fumarate) and polyethylene glycol covered by the invention of the present application are indicated by thick lines, while peaks due to typical additives (hydroxypropyl methyl cellulose phthalate, hydroxypropyl cellulose, low degree of substitution hydroxypropyl cellulose, NP-103_32_42, NP-108[200], polyvinylpyrrolidone, crospovidone, crystalline cellulose, ethyl cellulose, methacrylic acid copolymer, corn starch, mannitol, talc, triethyl citrate, and titanium oxide) are indicated by thin lines. The measurement conditions in this test example are given in Table 1.

TABLE 1

| Measurement instrument | XDS near infrared spectrometer (Nireco Corporation) |
|---|---|
| Measurement method | diffuse reflection |
| Wavelength measured | 400 to 2500 nm |
| Number of scans | 32 |

Figure 1:
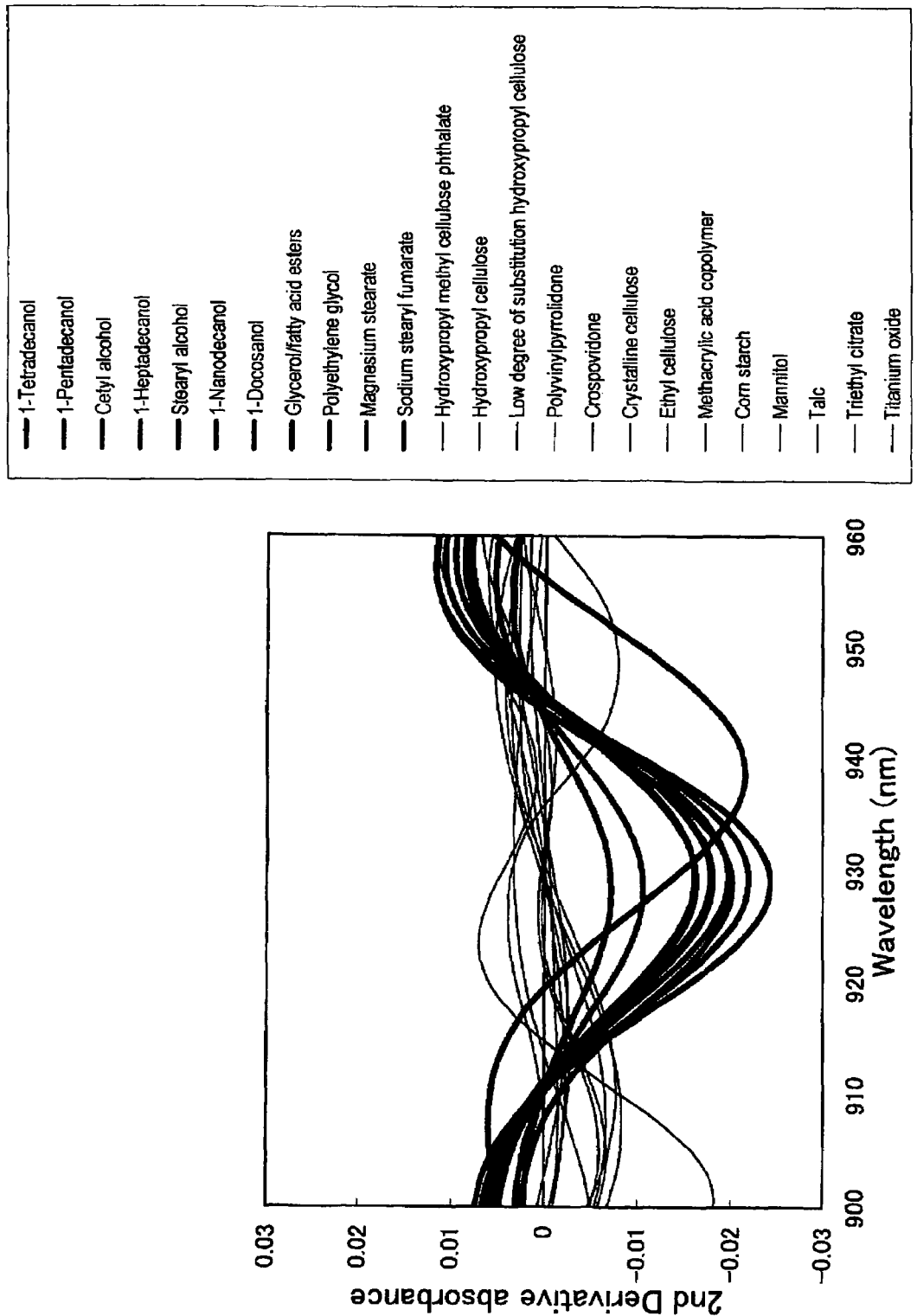
FIG. 1 shows the absorption of various components in a region of third overtone absorption due to long-chain hydrocarbyl-containing compounds and polyethylene glycol.
Figure 2:
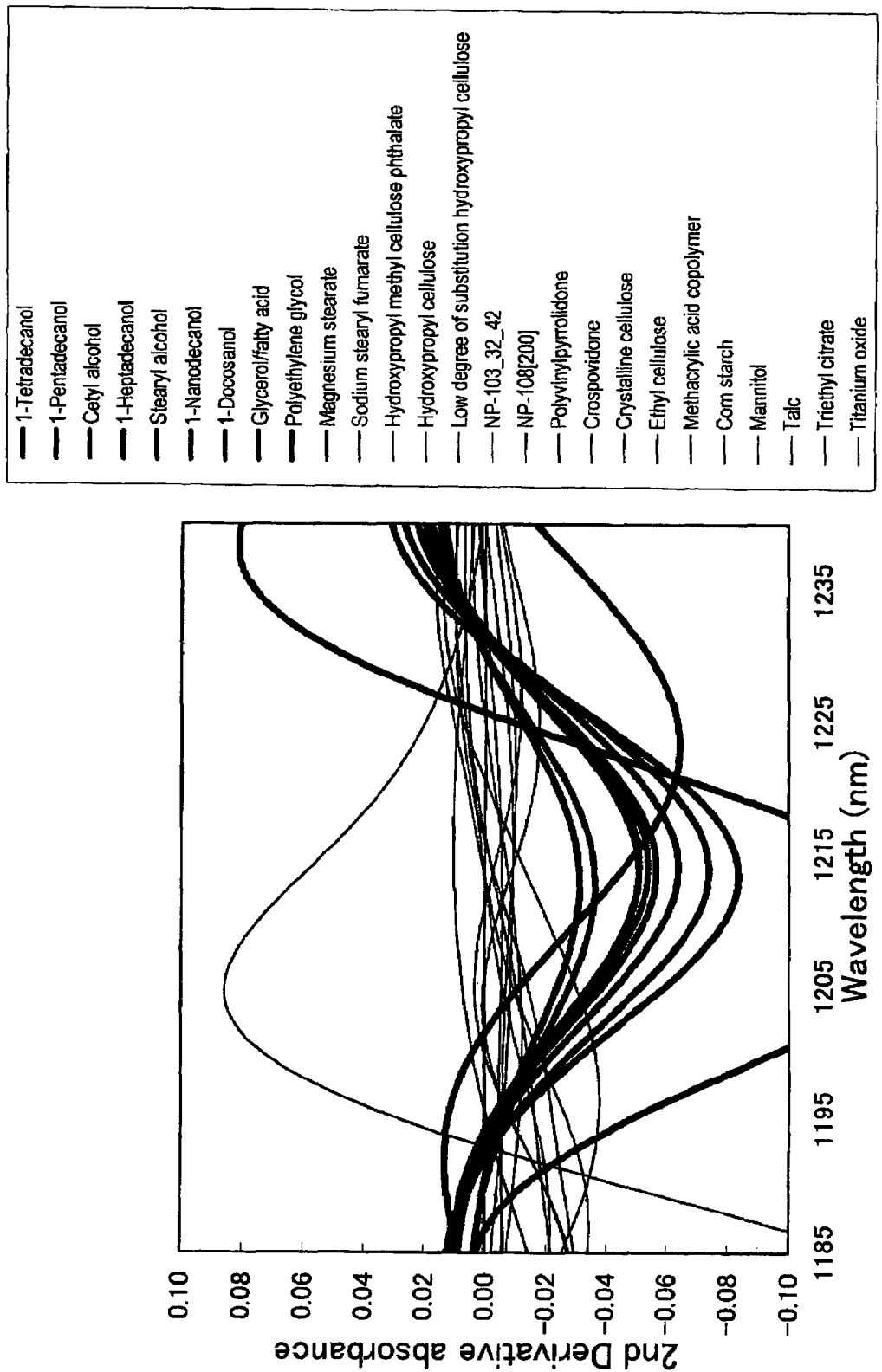
FIG. 2 shows the absorption of various components in a region of second overtone absorption due to long-chain hydrocarbyl-containing compounds and polyethylene glycol.
Figure 3:
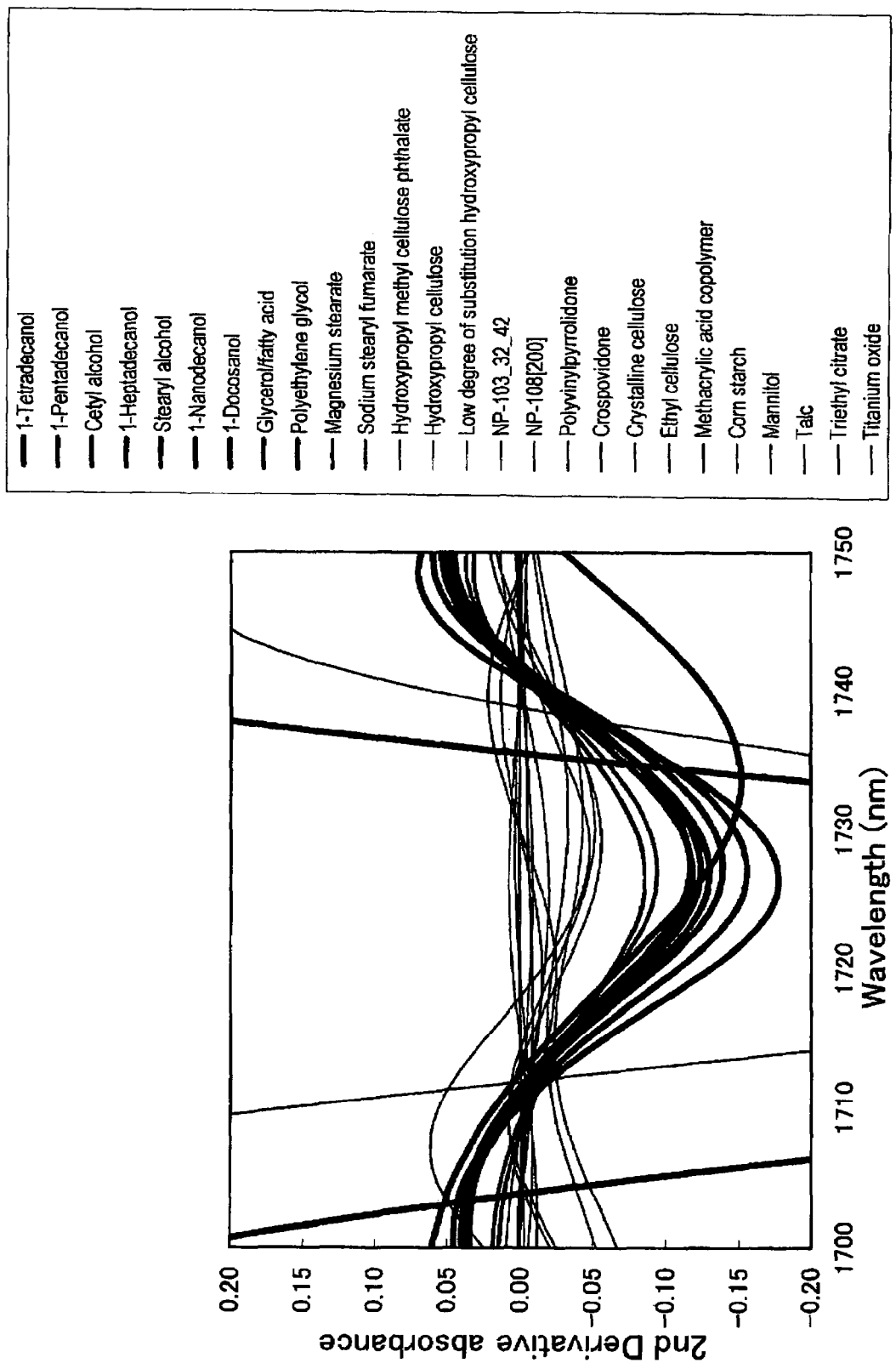
FIG. 3 shows the absorption of various components in a region of first overtone absorption due to long-chain hydrocarbyl-containing compounds and polyethylene glycol.
Figure 4:
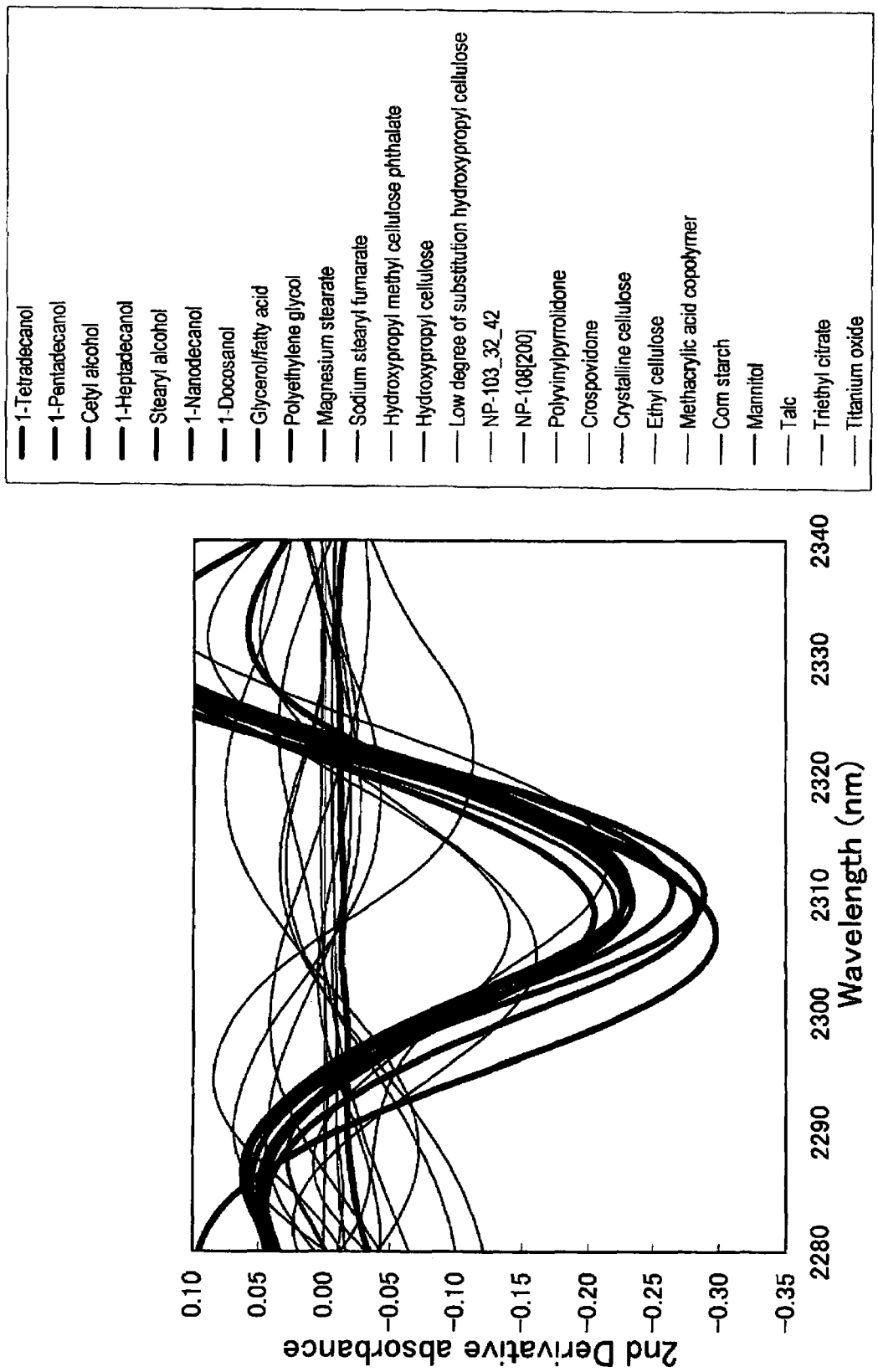
FIG. 4 shows the absorption of various components in a region of fundamental vibrations due to long-chain hydrocarbyl-containing compounds and polyethylene glycol.

As is clear from FIGS. 1 to 4, spectral peaks due to other ingredients are not seen in the region of third overtone absorption at 900 to 960 nm due to long-chain hydrocarbyl-containing compounds and polyethylene glycol (FIG. 1). In contrast, spectral peaks based on other ingredients were observed at 2280 to 2340 nm (FIG. 4), where fundamental vibrations are observed; at 1700 to 1750 nm (FIG. 3), where the first overtones of the fundamental vibrations are observed; and at 1185 to 1240 nm (FIG. 2), where the second overtones are observed. These results suggest that measurement using near infrared radiation in the neighborhood of 900 to 960 nm that is due to long-chain hydrocarbyl-containing compounds and polyethylene glycol makes possible a highly specific measurement that can inhibit the influence of spectra based on other components.

Test Example 2

Evaluation of the Coating Quantity

The coating quantity on tablets was evaluated using cetyl alcohol, a long-chain hydrocarbyl-containing compound that is generally used as a coating additive and whose use for pharmaceutical products has been recognized. In this test, 10, 15, 20, 25, or 30 mg of a coating liquid containing the components shown in Table 3 was coated by film coating on uncoated tablets having the constituent components shown in Table 2. The weight % of cetyl alcohol in the tablets was 0.46 to 1.37%. The coating quantity was calculated for 15 tablets at each level by subtracting the average weight of the 15 tablets prior to coating from the tablet weight of each single tablet after coating.

TABLE 2

| Main components X |
| Mannitol |
| Crospovidone |
| Hydroxypropyl cellulose |
| Sodium hydroxide |
| Sodium stearyl phthalate |
| Ethyl cellulose |
| Magnesium stearate |

TABLE 3

| Ethyl cellulose |
| Magnesium stearate |
| Methacrylic acid copolymer |
| Talc |
| Titanium oxide |
| Cetyl alcohol |
| Ethanol |

Measurement Conditions

The measurements in this test were carried out using the measurement conditions shown in Table 4.

TABLE 4

| Measurement instrument | XDS near infrared spectrometer (Nireco Corporation) |
|---|---|
| Measurement method | diffuse reflection |
| Wavelength measured | 400 to 2500 nm |
| Number of scans | 32 |

Absorption due to the acetyl group in cetyl alcohol was observed around 2310 nm (assigned to fundamental vibrations), around 1727 nm (assigned to the first overtone), around 1214 (assigned to the second overtone), and around 933 nm (assigned to the third overtone). Multiple linear regression (MLR) analysis was carried out at these wavelengths on the relationship between the actual coating quantity and the second derivative spectrum. The results are shown in Table 5.

TABLE 5

| Wavelengths measured | Correlation coefficient |
|---|---|
| 2310 | 0.7247 |
| 1727 | 0.9554 |
| 1214 | 0.9761 |
| 933 | 0.9925 |

Figure 5:
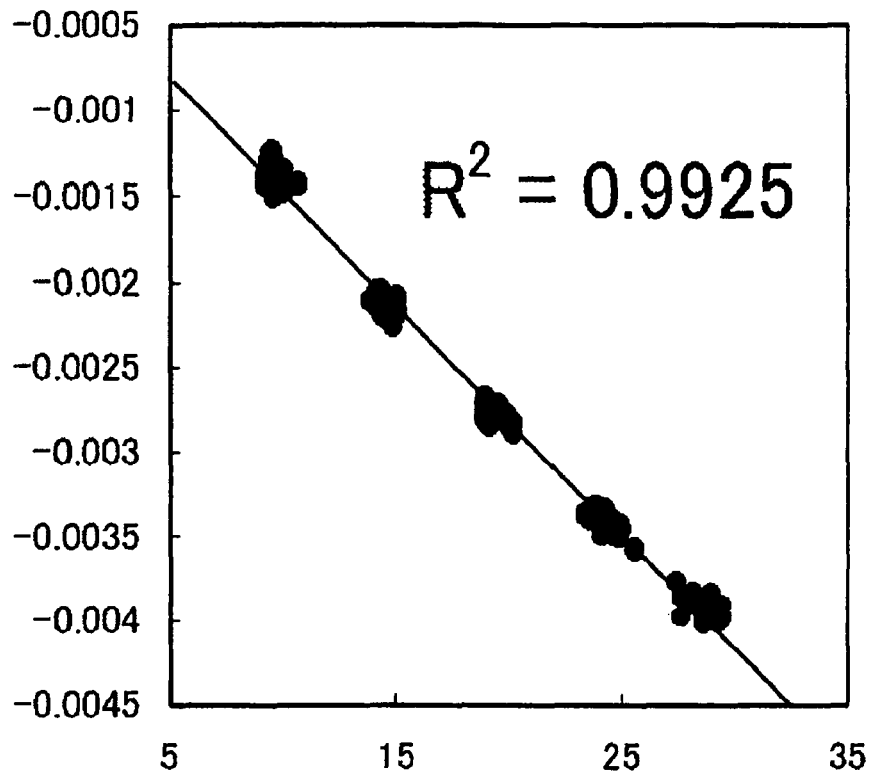
FIG. 5 is a graph of the correlation between the actual coating quantity and the coating quantity determined from the method of the present invention for measuring coating quantity.

As is clear from Table 5, the best correlation with the actual coating quantity was obtained at the wavelength of the absorption region for the third overtone (933 nm). A relationship with a very good correlation, as shown in FIG. 5, was observed at 933 nm for the correlation between the coating quantity and the absorption intensity in the near infrared spectrum. While, in terms of peak intensity, the absorptions at the wavelengths around 1214 nm, 1727 nm and 2310 nm are stronger than at the wavelengths around 933 nm, it is thought that the correlation with the actual coating quantity ends up being worse at the former wavelengths as a result of the influence of absorptions based on the other ingredient components listed in Tables 2 and 3. In contrast, it is thought that a good correlation with the actual coating quantity is obtained at the wavelengths around 933 nm because at these wavelengths there is a small influence from absorptions based on the other ingredient components. FIG. 5 contains the results of NIR measurements of 15 tablets for n=3, and the number of filled circles at each of the coating quantities of approximately 10, 15, 20, 25 and 30 mg is 45 (15 tablets×3).

Test Example 3

Evaluation of Dissolution Time

Figure 6:
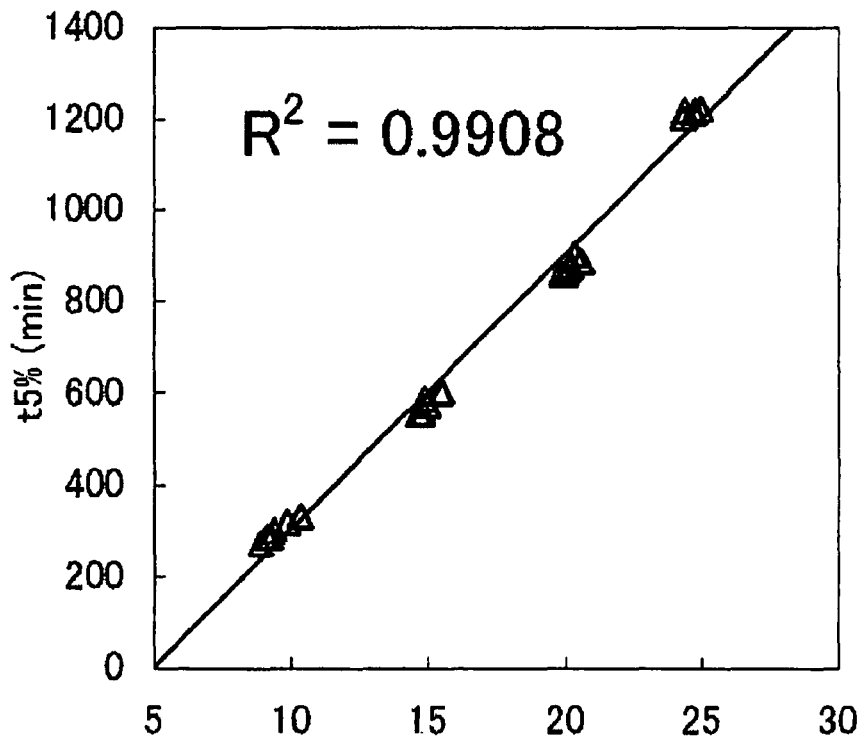
FIG. 6 is a graph of the relationship between the coating quantity obtained by the invention of the present application and the dissolution time.

The dissolution time was evaluated using the tablets employed in the preceding Test Example 2. These tablets were obtained by film coating 10, 15, 20, 25 or 30 mg of a coating liquid containing the components shown in Table 3 on uncoated tablets having the constituent components shown in Table 2, with the dissolution time of the pharmacologically effective component being controlled by the quantity of this film coating. The relationship between the time required for the dissolution rate of the pharmacologically effective component from the tablet to reach 5% (lag time) and the coating quantity obtained in Test Example 2 was investigated in this test. The results are shown in FIG. 6. The results are given for the execution of dissolution tests in 6 vessels, and the number of triangles in each case is 6.

As is clear from FIG. 6, a relationship with a good correlation was observed to exist between the lag time of the individual tablets and the method of measuring coating quantity according to the invention of the present application. This result suggests that the dissolution behavior can also be predicted by the method of measuring coating quantity according to the invention of the present application.

The invention claimed is:

1. A method of measuring the quantity of a coating applied to a drug product, comprising:
    measuring absorption or scattering of light of 800 to 1100 nm wavelength region by way of an additive which absorbs or scatters in the 800 to 1100 nm wavelength range and is coated on the drug product to obtain a measured value; and
    determining the quantity of coating applied to said drug product from said measured value.

2. The method according to claim 1, wherein the additive coated on the coating target is at least one compound selected from the group consisting of polyethylene glycol and long-chain hydrocarbyl-containing compounds.

3. The method according to claim 2, wherein the long-chain hydrocarbyl-containing compound is at least one compound selected from the group consisting of higher alcohols, fatty acid esters and fatty acid salts.

4. The method according to claim 1, wherein the additive is cetyl alcohol or stearyl alcohol.

5. A method of predicting the dissolution behavior of a pharmacologically effective component from a drug product, based on the coating quantity obtained by a method of measuring coating quantity which comprises:
    measuring absorption or scattering of light of 800 to 1100 nm wavelength region by way of an additive which absorbs or scatters in the 800 to 1100 nm wavelength range and is coated on the drug product to obtain a measured value;
    determining the quantity of coating applied to said drug product from said measured value; and
    predicting the dissolution behavior of the pharmacologically effective component based upon the coating quantity so determined.

* * * * *